United States Patent [19]
Pertinarides et al.

[11] Patent Number: 5,763,876
[45] Date of Patent: Jun. 9, 1998

[54] INLET HEATING DEVICE FOR ION MOBILITY SPECTROMETER

[75] Inventors: John Michael Alfred Pertinarides, Orlando, Fla.; Alexander Semenovich Tarassov, Mars, Pa.; Byron Lee Carnahan, Pittsburgh, Pa.; Charles W. Pipich, Monroeville, Pa.; Viktor Kouznetsov, Mars, Pa.

[73] Assignee: Mine Safety Appliances Company, Pittsburgh, Pa.

[21] Appl. No.: 627,584

[22] Filed: Apr. 4, 1996

[51] Int. Cl.$^6$ .............. B01D 59/44; H01J 49/00
[52] U.S. Cl. .................... 250/288; 250/286
[58] Field of Search ................ 250/286, 287, 250/288, 423 R

[56] References Cited

U.S. PATENT DOCUMENTS

| | | | |
|---|---|---|---|
| 4,732,046 | 3/1988 | Lawrence et al. | 250/287 |
| 5,037,611 | 8/1991 | Ledford | 250/288 |
| 5,218,203 | 6/1993 | Eisele et al. | 250/287 |
| 5,420,424 | 5/1995 | Carnahan et al. | 250/287 |
| 5,567,938 | 10/1996 | Mimura et al. | 250/288 |
| 5,611,846 | 3/1997 | Overton et al. | 96/102 |
| 5,663,560 | 9/1997 | Sakairi et al. | 250/288 |

*Primary Examiner*—Bruce Anderson
*Attorney, Agent, or Firm*—Titus & McConomy

[57] ABSTRACT

Generally, the present invention provides a device for heating the sample stream inlet of an ion mobility spectrometry (IMS) sensor. The heating device increases the temperature of the sample stream inlet surface to reduce the amount of time between adsorption and desorption taking place on the surface. This greatly improves the ability of the IMS sensor to follow rapidly changing analyte concentration levels. An alternate preferred embodiment of the present invention provides a flow smoothing device for decreasing the turbulence present in the fluid flow entering the IMS sensor's carrier stream inlet. This flow smoothing insert permits increasing the fluid flow rate entering the IMS sensor's carrier stream inlet to levels which maximize the IMS sensor's measurement sensitivity without causing mixing of the sample and carrier fluid stream flows.

23 Claims, 8 Drawing Sheets

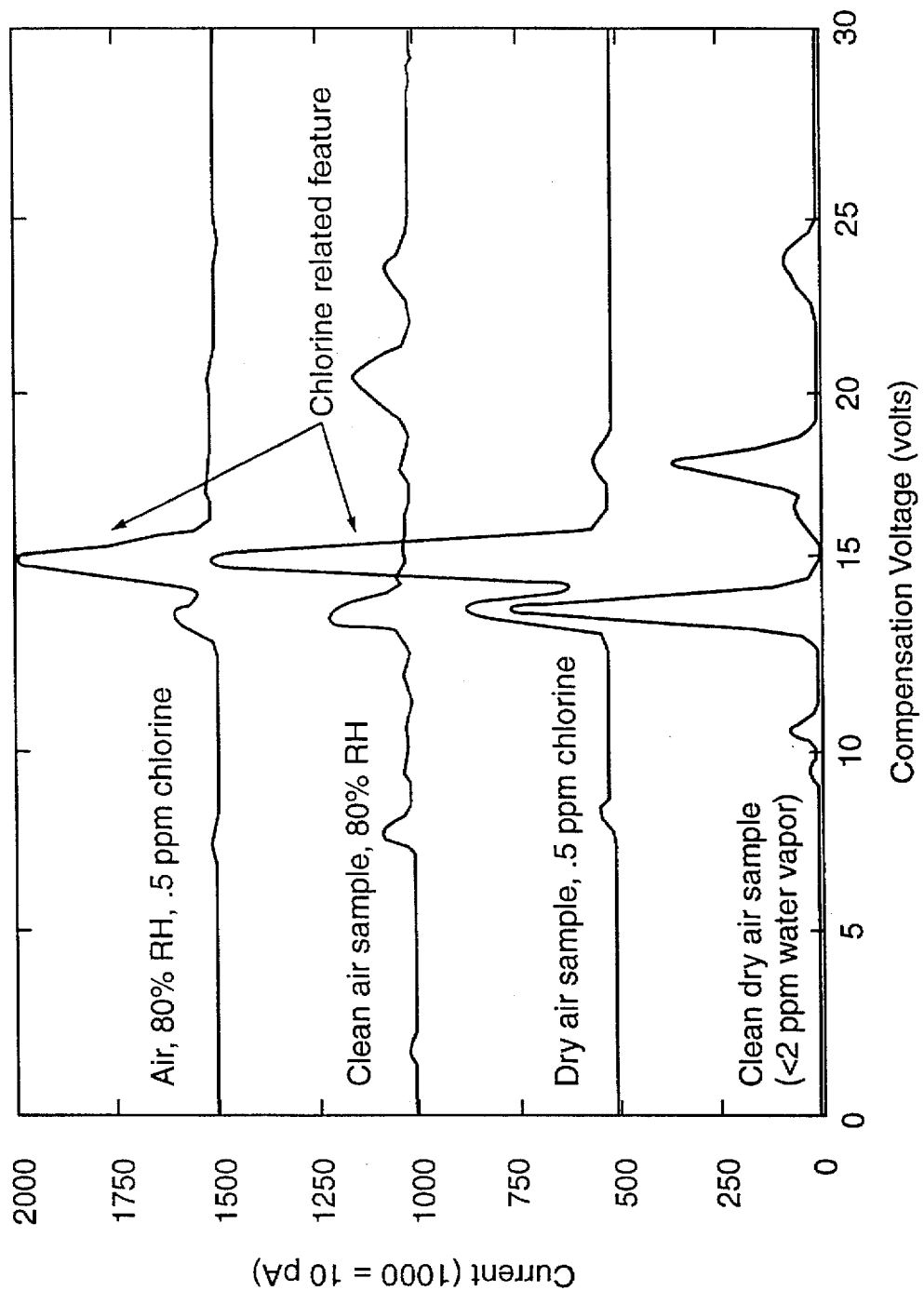

5,763,876

1

INLET HEATING DEVICE FOR ION MOBILITY SPECTROMETER

FIELD OF THE INVENTION

The invention relates generally to a device for heating the inlet of an ion mobility spectrometer (IMS), and specifically to a heated inlet device designed for use with a field ion mobility spectrometer.

BACKGROUND OF THE INVENTION

U.S. Pat. No. 5,420,424 provides a sensor using ion mobility spectrometry (IMS) to detect trace concentration level species present in a sample gas stream. The IMS disclosed in U.S. Pat. No. 5,420,424 utilizes periodic electrical fields to separate different species of ions according to the functional dependence of their mobility with electric field strength. Ions generated in the ionization chamber of the IMS sensor are guided through an ion filter to an ion detector by an electric field known as the "dispersion field." This "dispersion field" is created by an asymmetric periodic radio frequency (RF) voltage applied between a pair of closely spaced longitudinal electrodes. The displacement of the ions induced by the dispersion field is modified or compensated by a second electric field known as the "compensation field." The compensation field is created by an adjustable time independent direct current electrical potential that is applied between the electrodes to isolate a particular ion species for detection as a result of the variance in mobility between particular ion species as a function of electric field strength. This form of ion mobility spectrometry, known as field ion spectrometry (FIS) offers a new method of detecting species present at trace (parts per million to parts per trillion) concentration levels in a sample gas to be analyzed.

Currently available IMS sensors such as that disclosed in U.S. Pat. No. 5,420,424 could be improved by heating the IMS sensor surfaces which come into contact with the sample fluid stream as it enters the inlet of the sensor. Without heating, the sensor's ability to provide an accurate assessment of an ionizable contaminant's concentration in the sample stream when this species'concentration is changing rapidly with time is diminish ed. The lack of heating at the sample stream inlet results in absorption of analyte as the sample passes from the outside environment into the IMS sensor. This absorption win cause accumulation of the analyte on the sample stream inlet surface until an equilibrium density level is reached. The time it takes to reach this equilibrium density is directly dependent on the temperature of the sample stream inlet surface. Due to absorption of the analyte out of the sample as it traverses the sample stream inlet, the IMS will exhibit a diminished response to its ionization until the equilibrium density is reached. This diminished response will gradually disappear as the equilibrium density is approached. However, the ability of the IMS sensor to rapidly respond to constantly changing concentration levels of the analyte is reduced by this absorption phenomenon.

The present invention provides a device for significantly minimizing the effects of absorption taking place on the IMS sample stream inlet surface. This decreases the IMS sensor's response time and recovery time characteristics with regard to detecting rapidly changing analyte concentration levels. The device provides heating to the IMS sensor's sample stream inlet to increase the temperature of the sample stream inlet surface. This increased temperature results in less time between absorption and desorption of the analyte on the sample stream inlet surface, which causes a greater portion of the overall analyte concentration level to be detected by the IMS sensor. This results in a significant reduction in the time necessary for the analyte to reach equilibrium density on the sample stream inlet surface, thus decreasing the IMS sensor's response time and recovery time characteristics with regard to detecting rapidly changing concentration levels.

Additionally, the present invention preferably provides a flow smoothing insert for reducing the turbulence in the fluid stream flow entering the IMS sensor's carrier stream plenum inlet. Elimination of this turbulence is necessary in order to prevent mixing of the carrier and sample fluid streams in the ion filter, which would otherwise adversely affect the IMS sensor's sensitivity due to the impurities present in the sample fluid stream. Without the use of a flow smoothing insert, a reduction of the carrier stream flow is necessary to eliminate this turbulence, which in turn adversely affects the IMS sensor's sensitivity. This decreased sensitivity is caused by the increased amount of time required for the ionized substance to traverse the ion filter. Extending the time interval which ions spend in the ion filter allows more time for loss mechanisms (such as diffusion to the filter's walls and charge neutralization reactions) to attenuate the ion current which reaches the ion detector. The present invention provides a device for reducing turbulence in the carrier stream flow, allowing a return of the flow to a level that restores the IMS sensor's sensitivity.

Accordingly, the present invention provides a device for significantly lessening the amount of time between absorption and desorption taking place on the IMS sample stream inlet surface to decrease the IMS sensor's response time and recovery time characteristics, thus permitting the device to more accurately assess rapidly changing analyte concentration levels.

Accordingly, the present invention preferably provides a device for heating the IMS sample stream inlet to increase the temperature of the sample stream inlet surface thereby reducing the amount of time between absorption and desorption taking place on the surface. The present invention also preferably provides a device for decreasing the turbulence present in the fluid flow entering the IMS carrier stream plenum inlet. The present invention also preferably provides a device for increasing the fluid flow rate entering the IMS sensor's analytical gap to levels which restores IMS sensor's sensitivity without causing mixing of the sample and carrier fluid stream flows.

SUMMARY OF THE INVENTION

Generally, the present invention provides a device for heating the sample stream inlet of an ion mobility spectrometry (IMS) sensor. The heating device increases the temperature of the sample stream inlet surface to reduce the amount of time between absorption and desorption taking place on the surface. This significantly improves the ability of the IMS sensor to follow rapidly changing analyte concentration levels. The inlet heating device comprises a hollow metal passageway for passage of a sample fluid stream from the outside environment into the sample stream inlet of the ion mobility spectrometer. A hollow metal housing is preferably hermetically welded to both the passageway inlet and outlet ends for mounting the device to the sample stream inlet of the ion mobility spectrometer using a ceramic flange. A heating element preferably comprised of a high resistance wire surrounds the surface of the passageway for electrically heating the passageway. A temperature control circuit controls electrical power input to the heating element to maintain the passageway at a substantially constant reference value. The temperature control circuit comprises at least one temperature measuring device, preferably an electrical resistance-measuring thermometer, attached to the surface of the passageway for measuring the temperature of the passageway. A temperature controller having an input electrically connected to the temperature measuring device and an output electrically connected to the heating element compares the temperature measured by the temperature measuring device to a predetermined reference value and adjusts the electrical power input to the heating element to substantially match the temperature of the passageway to the reference value.

An alternate preferred embodiment of the present invention provides a flow smoothing device for decreasing the turbulence present in the fluid flow entering the IMS sensor's carrier stream inlet. This flow smoothing insert permits increasing the fluid flow rate entering the IMS sensor's carrier stream inlet to levels which maximize the IMS sensor's measurement sensitivity without causing mixing of the sample and carrier fluid stream flows. The flow smoothing element comprises an insert of porous material, preferably a disc-shaped metal mesh with a center opening that fits over the housing of the heating device, which is placed between the heating device housing and the surface of the sample stream inlet at a location proximate to the outlet end of the heating device. The flow smoothing insert fills the gap between the heating device housing and the sample stream inlet plenum surface, causing the velocity of the fluid stream flow entering the carrier stream inlet to be equalized across the outlet side of the flow smoothing element to eliminate flow turbulence. Preferably, the flow smoothing insert is electrically isolated from the IMS sample stream inlet plenum surface by a band of electrically insulating material placed between the insert and the sample stream inlet surface.

Other details, objects, and advantages of the present invention will become apparent in the following description of the presently preferred embodiments.

BRIEF DESCRIPTION OF THE DETAILED DRAWINGS

In the accompanying drawings, the preferred embodiments of the present invention and preferred methods of practicing the present invention are illustrated wherein:

FIG. 7B shows the increased sensitivity of an IMS measurements with a flow smoothing insert attached to the heating device as in the alternate preferred embodiment of the present invention.

DETAILED DESCRIPTION OF THE PREFERRED EMBODIMENT

Figure 1:
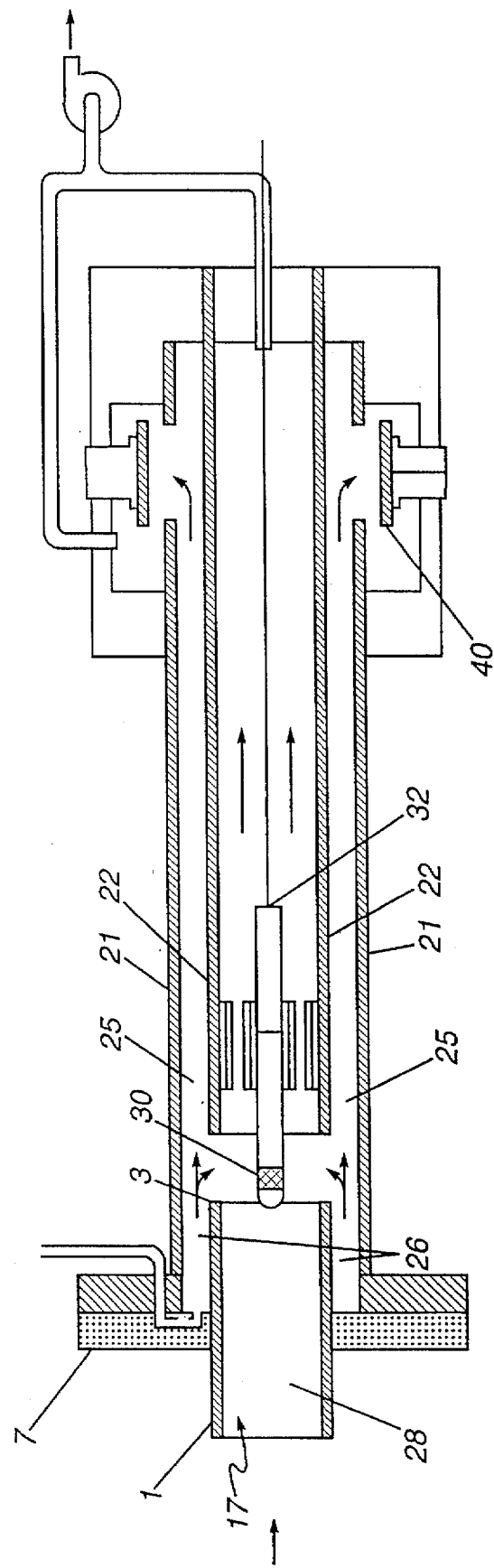
FIG. 1 is a cross-sectional view of an ion mobility spectrometer for use with the present invention.

FIG. 1 shows a cross-sectional view of the IMS sensor device described in U.S. Pat. No. 5,420,424, the disclosure of which is incorporated herein by reference. The IMS sensor draws a sample fluid stream containing the analyte into the ionization chamber 28 through inlet 17. As described in U.S. Pat. No. 5,420,424, the analyte is ionized by the ionizer 30 while flowing through the ionization chamber 28 and then directed into the analytical gap 25 under the influence of a radial electric field created by a bias potential applied to electrode 32. The ionized analyte traverses the analytical gap 25 to the ion detector 40 under the influence of the dispersion field and the compensation field produced between electrodes 21 and 22. Under proper biasing conditions and at analyte concentration levels to be measured, the signal produced by the ion detector 40 will be proportional to the concentration level of the selected analyte in the sample fluid stream.

Figure 2:
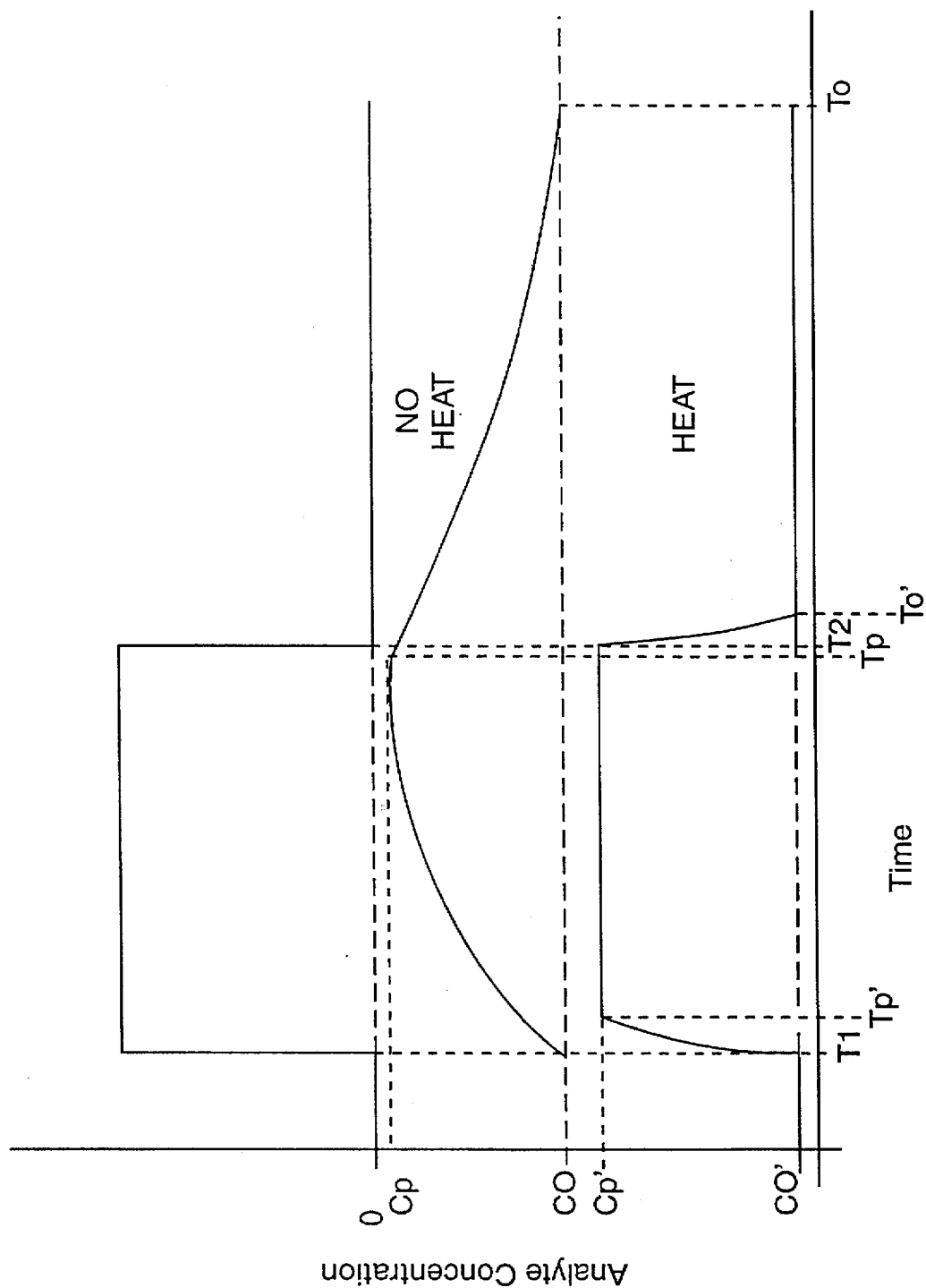
FIG. 2 is a simplified representation of an IMS sensor's response time and recovery time characteristic in detecting a stepwise increase in the concentration of the analyte with and without heating of the ionization chamber inlet.

FIG. 2 shows a simplified representation of the IMS sensor's response time and recovery time characteristic to a stepwise increase and decrease in the concentration of the analyte with and without heating of the ionization chamber inlet 17. As can be seen from FIG. 2, the IMS sensor's response exhibits a time lag from the point T1 when the concentration is increased to the point Tp when the IMS sensor's response initially reaches its peak value Cp. This time lag is due to absorption of the analyte on the ionization chamber 28 surface as the sample passes from the outside environment into the IMS sensor. This absorption results in less of the analyte being available for ionization and detection than is actually present in the sample. The peak IMS sensor response Cp is obtained when the concentration level of the analyte on the ionization chamber 28 surface has achieved an equilibrium density that corresponds to the increased concentration level of the analyte present in the sample. At the time Tp when the equilibrium density is reached, absorption of the analyte taking place on the IMS sensor's sample stream inlet surface is balanced by desorption of the analyte from the sample stream inlet so that no net absorption of the analyte is occurring. This causes the full amount of the analyte entering the ionization chamber 28 to be available for ionization and detection by the IMS sensor.

The increase in the analyte concentration is eliminated at a point in time T2 very soon after the equilibrium point Tp is reached. This stepwise decrease in the original concentration level causes the reverse effect to take place and results in an additional time lag until the original analyte concentration level Co is detected by the IMS sensor at time To. In that case gradual release of the desorbed analyte from the ionization chamber surface 28 results in more of the analyte being available for ionization and detection than is actually present in the sample. The original IMS sensor response Co is obtained when the concentration level of the analyte on the ionization chamber 28 surface has returned to the equilibrium density corresponding to the original concentration level of the analyte present in the sample.

The time lag in either case is directly dependent on the temperature inside the IMS sensor inlet 17. A greater temperature results in less time between absorption and desorption taking place on the ionization chamber 28 surface and a consequently smaller period of elapsed time until equilibrium is reached.

Figure 3:
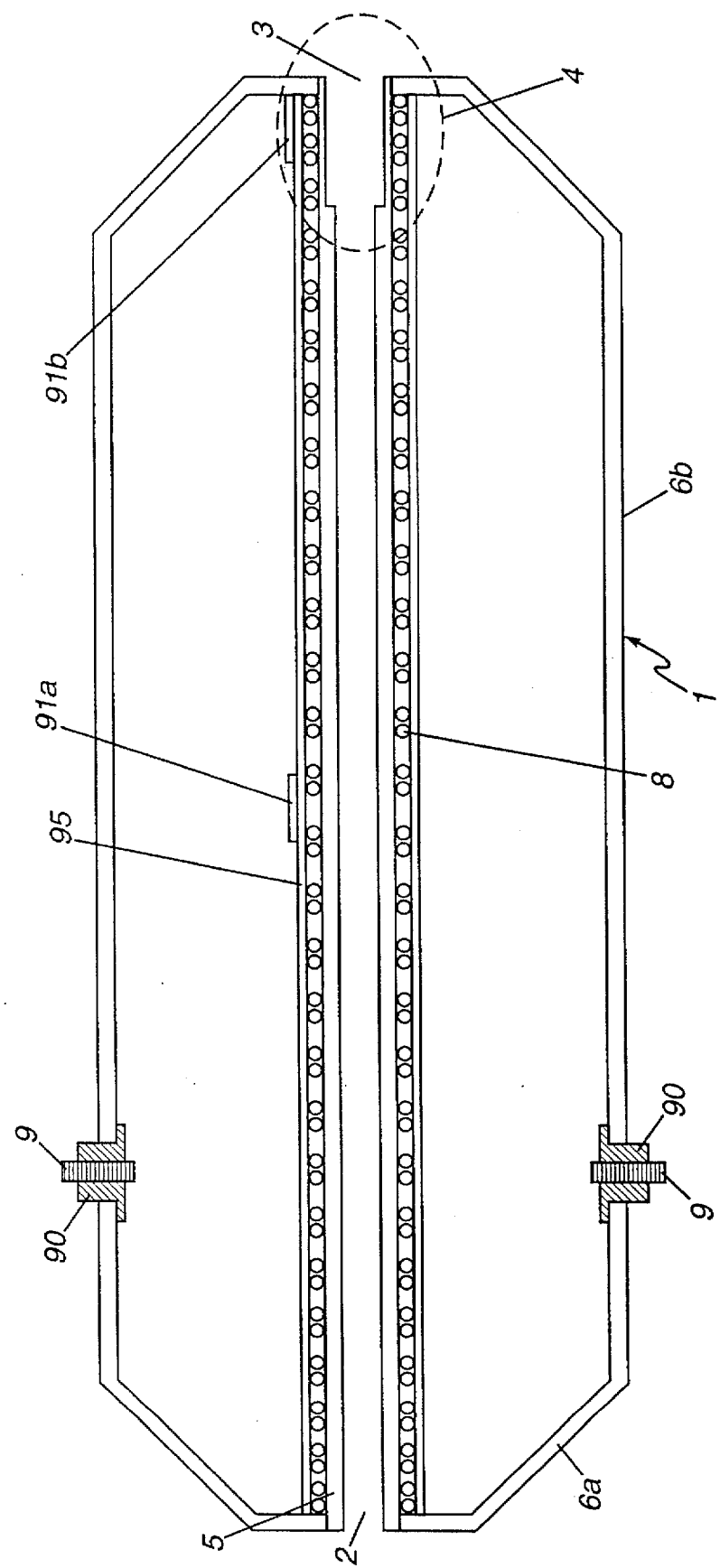
FIG. 3 is a cross-sectional view of a preferred embodiment of the heating device of the present invention.

The preferred embodiment of the invention shown in FIG. 3 provides a heating device 1 for increasing the temperature inside the IMS sensor inlet 17 to minimize the time lag experienced in the detection of a change in analyte concentration level. As shown in FIG. 1, the inlet heating device 1 is located inside the inlet 17 of the IMS sensor forming a passageway from the inlet 17 to the ionizer 30 that defines the ionization chamber 28. As shown in FIGS. 1 and 3, the heating device 1 has an inlet end 2 in direct communication with the outside environment and an outlet end 3 with a counterbore 4 that houses the ionizer 30. The sample stream travels through a passageway 5 that spans the region between the inlet end 2 and outlet end 3. The passageway 5 preferably has a surface defined by a cylindrical tube shape and preferably made of a metal such as titanium, stainless steel, gold, nickel or other chemically stable metals having an inherently low vapor pressure characteristic. Other non-metallic materials are possible for the passageway 5, including glass, quartz, sapphire, teflon or other low porosity, low vapor pressure non-chemically reactive materials. The heated passageway 5 is enclosed by two hollow shells 6a and 6b, both also preferably made of a metal such as titanium, stainless steel, gold, nickel or other chemically stable metals having an inherently low vapor pressure characteristic. The hollow shells 6a and 6b are each preferably bonded to an opposite end 2 or 3 of the passageway 5 surface by techniques such as laser welding, electron beam welding, glass-to-metal seals, ceramic-to-metal seals, soldering, brazing, and adhesive sealing to form a hermetic seal between the interior of the shells 6a and 6b and the passageway 5. In addition, other methods of attaching the hollow shells 6a and 6b to the passageway 5 are possible, such as metal swaging, interference fitting, and heating shrinking. The space between the passageway 5 and the inner surface of the hollow shell 6a or 6b is preferably filled with a fiber insulating material such as kaowool, asbestos, fiberglass or a ceramic material. As shown in FIG. 1, the housing formed by the mated heating device shells 6a and 6b is preferably mounted to the IMS inlet 17 on a mounting flange 7 of non-metallic material, such as a ceramic, that ensures a gas-tight thermal barrier between the interior of the heated passageway 5 and the interior of the IMS sensor. The flange 7 can be made of a metal in embodiments for the passage way 5 and shells 6a and 6b that use non-metallic materials.

As shown in FIG. 3, the preferred embodiment has a heating element 8 of insulated, high resistance wire, preferably 0.02 inch diameter tetraflouroethylene (TFE)-coated Constantan thermocouple wire, wound around the heated passageway 5 from the inlet end 2 to the outlet end 3 to provide electrical heating to the passageway 5. Other metals such as platinum that can be formed as a thin film surrounding the passageway 5 could be used for the heating element 8. In addition, a flexible heating element 8 in which the thin metal film is embedded in a material such as a clear polyimide film, a fiber paper aramide, or silicon rubber could be used. Additionally, the thin metal film heating element 8 could be embedded in a rigid mica shell. The heating element 8 of the preferred embodiment is wound in dual-helix fashion around the passageway 5 and is joined to at least one contact pin 9 that energizes the heating element 8. Preferably, a plurality of contact pins 9, made of #2–56 stainless steel all-thread rod, are both mounted in a single ring 90 of insulating material such as Kel-F plastic that is embedded between the metal shells 6a and 6b during the welding process. In the preferred embodiment, a layer of teflon tape 95 preferably holds the heating element 8 against the passageway 5 to improve heat transfer efficiency between the heating element 8 and the passageway 5. To provide a more uniform temperature profile across the length of the passageway 5, the winding density (or pitch) of the heating element 8 in the preferred embodiment is increased near the heating device inlet end 2 and outlet end 3 where heat losses are at their maximum.

Figure 4:
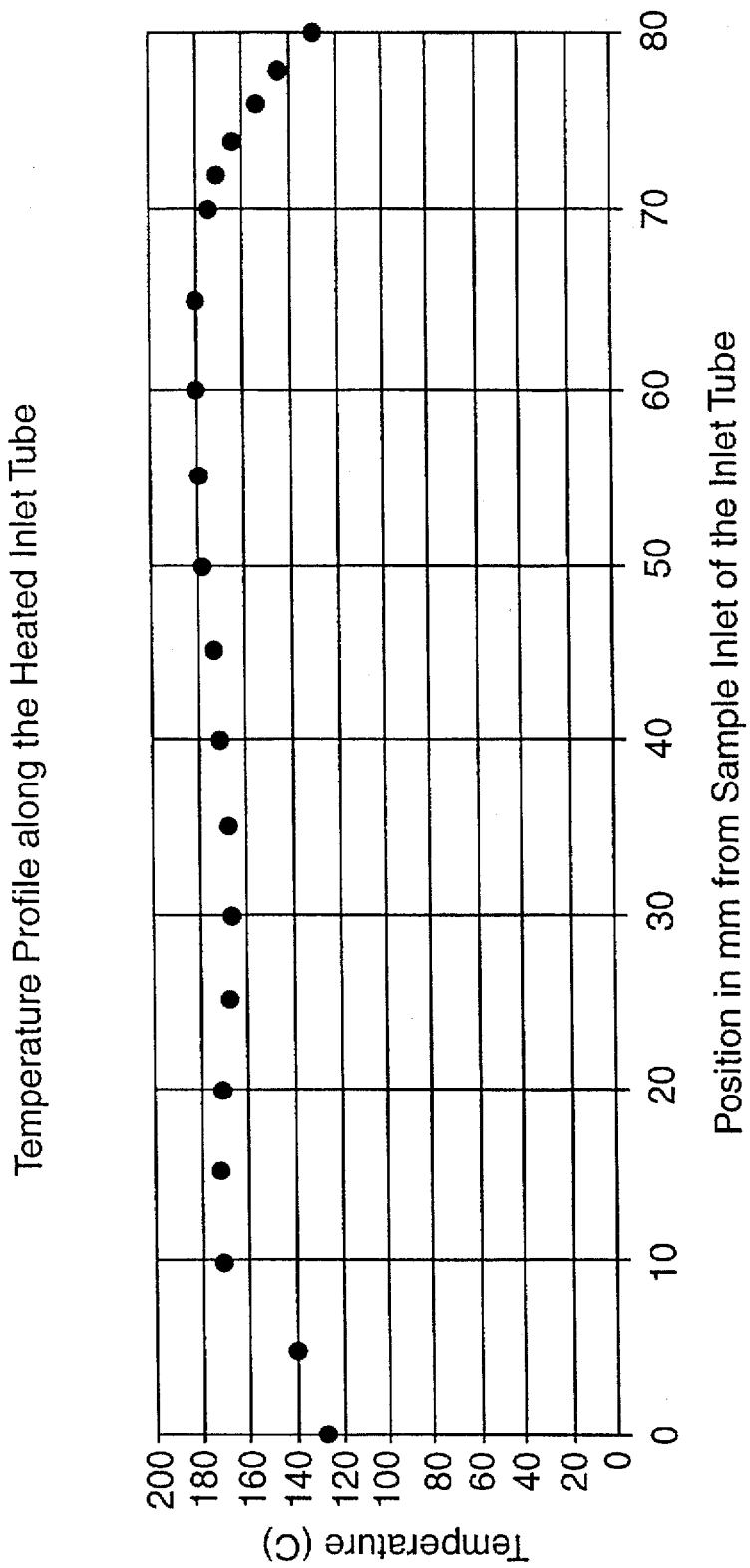
FIG. 4 is a graph of the temperature profile across a heating device of the present invention.

Two platinum resistance thermometers 91a and 91b, each preferably a Minco Thermal-Ribbon resistance-measuring thermometer Model No. S651PDZ24A, are attached to the heated passageway 5 to monitor the temperature of the passageway 5. Other components which could be used for the thermometers 91a and 91b are a thermocouple, a thermistor, and a semiconductor. A primary thermometer 91a is positioned near the midpoint of the passageway 5 while a backup thermometer 91b is positioned near the outlet end 3. The thermometers 91a and 91b are connected to a temperature controller 92 which switches power to the heating element 8 through the contact pins 9 to maintain a substantially uniform temperature profile across the heated passageway 5. A conventional resistance-measuring temperature controller 92, preferably a MINCO Model No. CT-149, compares the temperature measured by the thermometer 91a or 91b to a selected setpoint temperature programmed into the temperature controller 92. The backup thermometer 91b is only used in the event of a failure of the primary thermometer 91a or the temperature controller 92. The temperature comparison can be performed by means of an algorithm run on a computer processor by computer software programmed for this purpose that is stored on a computer-readable storage medium. Other means of performing the temperature comparison are also possible, such as use of an electronic integrated differential amplifier circuit, an analog or a combined analog and digital comparison circuit comprised of discrete electrical and digital logic components, or other similar circuitry presently in the state of the art. As shown in FIG. 4, the temperature control circuitry in the preferred embodiment results in a stabilized temperature profile across the heated passageway 5.

Figure 5:
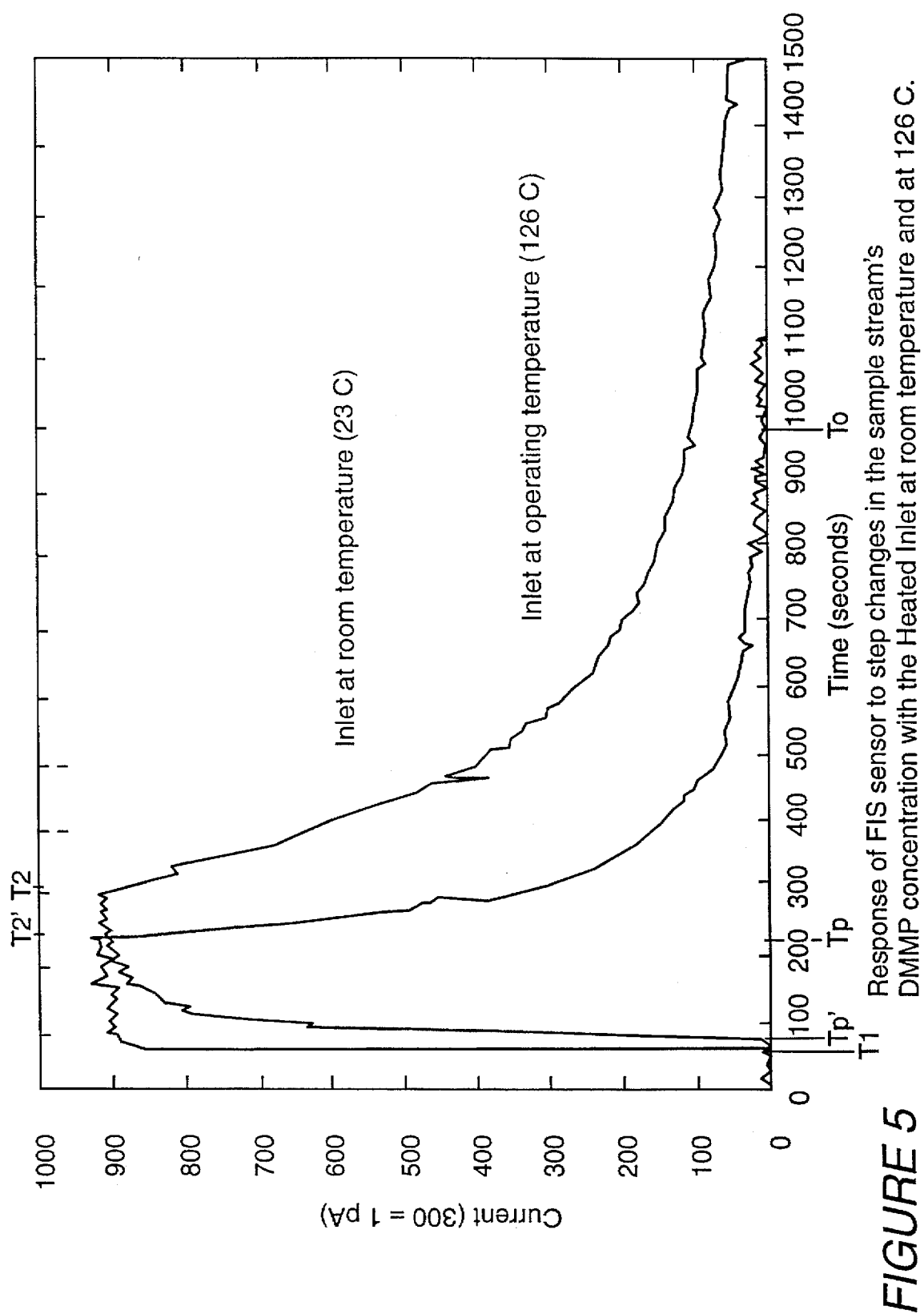
FIG. 5 is a graph illustrating the effect of an inlet heating device of the present invention on an IMS sensor's response time and recovery time characteristic to changes in analyte concentration levels.

FIG. 5 illustrates the effect of the inlet heating device 1 on the IMS sensor's response to changes in analyte concentration levels. The use of the heating device 1 to heat the IMS inlet 17 to a typical operating temperature (approximately 126C) causes an approximately tenfold improvement in the IMS sensor's response time when compared to maintaining the inlet 17 at room temperature (as indicated by the time interval from T1 to Tp' with use of the heating device 1 as opposed to the time interval from T1 to Tp without the heating device 1 installed). As can be seen from FIG. 5, the IMS sensor's recovery time characteristic is also improved by use of the inlet heating device 1 (as indicated by the time interval from T2' to To with use of the heating device 1 as opposed to the time interval from T2 to a point beyond the end of the graph without the heating device 1 installed).

In order to prevent degradation of the IMS sensor's sensitivity, mixing of the carrier and sample fluid stream flows must be prevented as the carrier stream enters the analytical gap 25 from the IMS carrier stream plenum 26. This is necessary in order to prevent impurities present in the sample fluid stream from entering the analytical gap and adversely affecting the ion detector 40 measurement. To achieve the segregation of carrier and sample stream flows, the amount of flow entering the IMS carrier stream plenum 26 typically exceeds the portion of the carrier stream flow entering the analytical gap 25 by 1 to 1.5 liters per minute.

However, in order to prevent degradation of the sensitivity (i.e. change in signal amplitude per unit change in analyte concentration), the plenum 26 carrier stream flow must be on the order of 3 to 4 liters per minute. Lowering this flow level results in additional time for the ions to traverse the analytical gap 25 to the ion detector 40, which permits more of the ions to migrate to the analytical gap 25 walls due to diffusion or to undergo charge neutralization reactions and thus escape measurement by the detector 40. Use of the inlet heating device 1 shown in FIGS. 1 and 3 makes it difficult to prevent a degradation in the sensitivity of the IMS sensor's response while at the same time avoiding mixing of the carrier and sample stream flows, since the maximum plenum 26 carrier stream flow possible without causing mixing is approximately 1.8 liters per minute. Mixing is caused at higher carrier stream flow levels due to the turbulence created by the blunt shape of the heating device outlet end 3.

Figure 6:
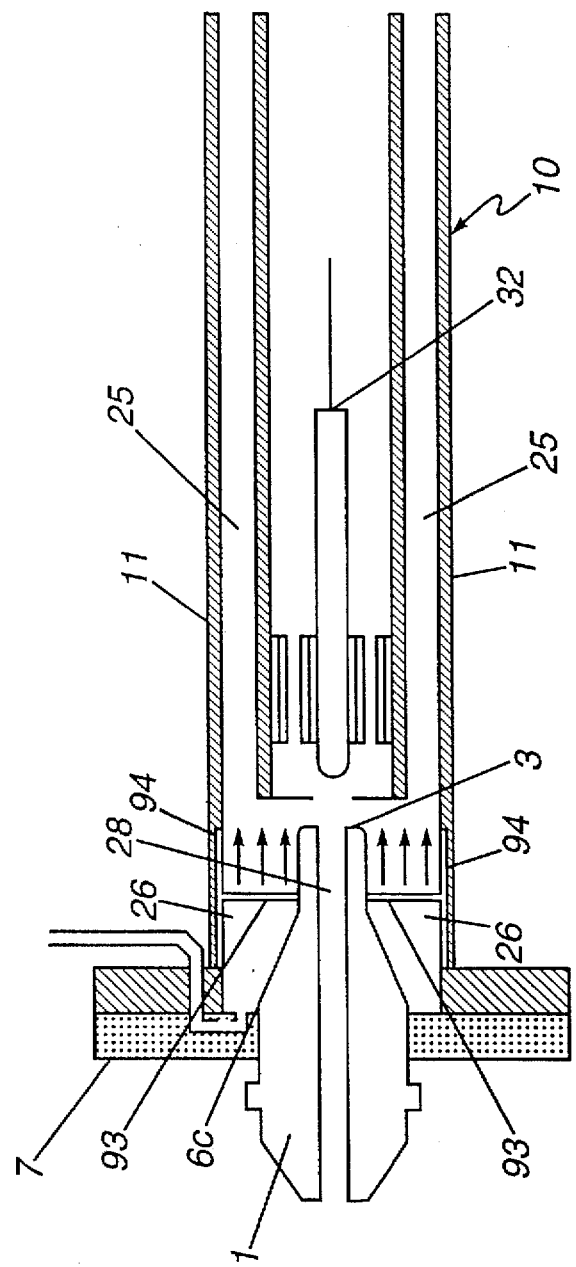
FIG. 6 is a cross-sectional view of an alternate preferred embodiment of a heating device configured with a flow smoothing insert.

As shown in FIG. 6 a flow smoothing insert 93 can be placed in the gap between a heating device shell of revised shape 6c and the inner surface of the IMS housing 11 to eliminate the turbulence created by the heating device outlet end 3. The revised shape of the shell 6c reduces the gap between the IMS housing 11 inner surface and the shell 6c at the mounting flange 7 while gradually increasing this gap closer to the heating device outlet end 3. The flow smoothing insert 93 is preferably made of a fine pitch stainless steel mesh shaped in the form of a round disc with a center opening concentric with the outer circumference of the disc. Other possible materials for the flow smoothing insert 93 are titanium, stainless steel, gold, nickel and other non-reactive metals having an inherently low vapor pressure characteristic. Other low porosity, low vapor pressure non-reactive, non-metallic materials such as glass, quartz, teflon and sapphire can be used for the flow smoothing insert 93. The flow smoothing insert 93 is slipped over the heating device outlet end 3 to form an interference fit with the heating device shell 6c prior to mounting the heating device 1 on the IMS sensor. When the heating device 1 is mounted on the IMS sensor the flow smoothing insert 93 will fill the gap between the heating device shell 6c and the IMS housing 11 inner surface at a location proximate to the heating device outlet end 3. Since the surface of the heating device shell 6c is electrically connected (not shown) to electrode 32 to contribute to the radial electric field created by the bias potential applied to electrode 32, the flow smoothing insert 93 must be electrically insulated from the grounded IMS housing 11. This is accomplished by placing a band 94 of electrically insulating material such as teflon between the flow smoothing insert 93 and the IMS housing 11 inner surface.

Figure 7A:
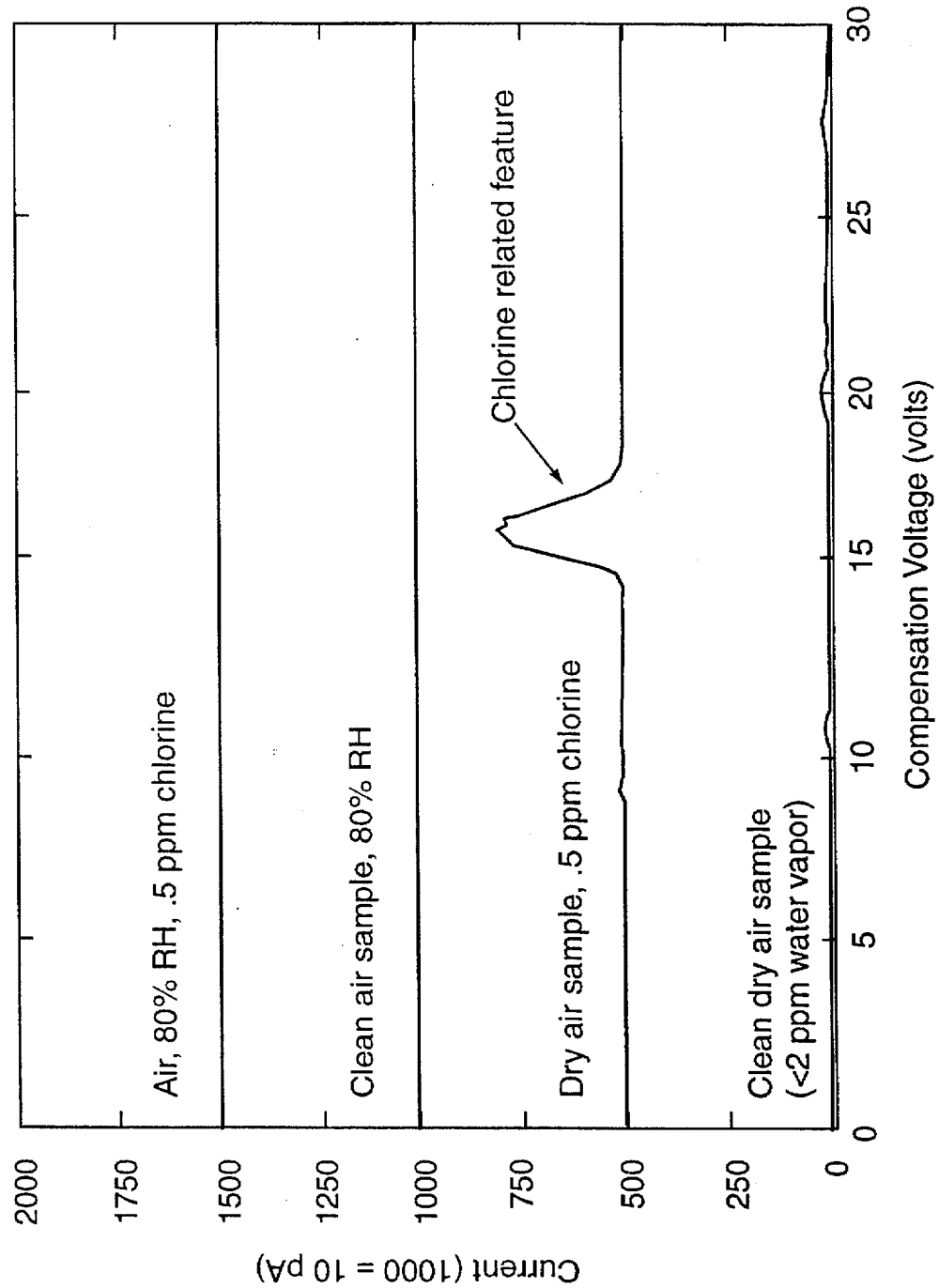
FIG. 7A shows a typical set of data collected by an IMS sensor without a flow smoothing insert attached to the heating device.

After the inlet heating device 1 is mounted on the IMS sensor with the flow smoothing insert 93 attached, the flow entering the carrier stream plenum 26 will undergo gradual volume expansion before being filtered through the flow smoothing insert 93. This gradual volume expansion in combination with the filtering will produce a laminar carrier stream flow profile throughout the volume between the heating device outlet end 3 and the IMS housing 11 upon exit of the carrier flow stream from the flow smoothing insert 93. This laminar flow profile prevents the sample stream from being mixed with the portion of the carrier stream entering the analytical gap. This in turn will allow increasing the flow entering the carrier stream plenum 26 so that losses in IMS sensitivity due to ion diffusion in the analytical gap are minimized. FIG. 7B shows the increased sensitivity of the IMS sensor's response with the flow smoothing insert 93 attached to the heating device 1 as compared to the IMS sensor's measurements without the flow smoothing insert 93 shown in FIG. 7A.

While presently preferred embodiments of practicing the invention has been shown and described with particularity in connection with the accompanying drawings, the invention may otherwise be embodied within the scope of the following claims.

What is claimed is:

1. A device for heating a fluid stream entering the sample stream inlet of an ion mobility spectrometer, comprising:
   A. a hollow passageway having an inlet end in communication with an outlet end for passage of a sample fluid stream from the outside environment into the sample stream inlet;
   B. a hollow housing attached to both the passageway inlet and outlet ends for mounting the device to the sample stream inlet of the ion mobility spectrometer;
   C. an electrical heating element surrounding the surface of the passageway for heating the passageway; and
   D. a temperature control circuit for controlling electrical power input to the heating element, comprising:
      (i) at least one temperature measuring device attached to the surface of the passageway for measuring the temperature of the passageway;
      (ii) a temperature controller having an input electrically connected to the temperature measuring device and an output electrically connected to the heating element for:
         (a) comparing the temperature measured by the temperature measuring device to a predetermined reference value; and
         (b) adjusting the electrical power input to the heating element to substantially match the temperature of the passageway to the reference value.

2. The heating device of claim 1, wherein the passageway is made of a metal selected from the group consisting of titanium, stainless steel, nickel, gold and other non-reactive metals having an inherently low vapor pressure characteristic.

3. The heating device of claim 1, wherein the passageway is made of a material selected from the group consisting of glass, quartz, teflon, sapphire and other low porosity, low vapor pressure non-chemically reactive non-metallic materials.

4. The heating device of claim 1, wherein the housing is comprised of a pair of metal sections each welded to an opposite end of the passageway wherein both sections are made of a metal selected from the group consisting of titanium, stainless steel, nickel, gold and other non-reactive metals having an inherently low vapor pressure characteristic.

5. The heating device of claim 1, wherein the housing is made of a material selected for the group consisting of glass, quartz, teflon, sapphire and other low porosity, low vapor pressure non-chemically reactive non-metallic materials.

6. The heating device of claim 1, wherein the housing is attached to the passageway to form a hermetic seal between the housing and the passageway.

7. The heating device of claim 6, wherein the housing is attached to the passageway by a method selected from the group consisting of laser welding, electron beam welding, ceramic-to-metal sealing, glass-to-metal sealing, soldering, brazing, adhesive sealing, metal swaging, interference fitting and heating shrinking.

8. The heating device of claim 1, wherein the space between the passageway and the housing is filled with a heat insulating material.

9. The heating device of claim 8, wherein the insulating material is selected from the group consisting of kaowool, fiberglass, asbestos and a ceramic.

10. The heating device of claim 1, wherein the housing is attached to a flange mounted to the sample stream inlet to form a gas-tight attachment between the device and the sample stream inlet.

11. The device of claim 1, wherein the heating element comprises a high resistance metal wire wound around the passageway from the inlet end to the outlet end.

12. The heating device of claim 11, wherein the density of the winding is increased at both ends of the heating element.

13. The device of claim 1, wherein the heating element comprises thin metal film embedded in a material selected from the group consisting of a thin metal film, a clear polyimide film, a fiber paper aramide, silicon rubber and mica.

14. The device of claim 1 wherein the temperature measuring device is selected from the group consisting of an electrical resistance measuring thermometer, a thermocouple, a thermistor and a semiconductor.

15. The heating device of claim 1, wherein the temperature controller is a device selected from the group consisting of a computer processor, an electronic integrated differential amplifier circuit, an analog comparison circuit comprised of discrete electrical components and a combined analog and digital comparison circuit comprised of discrete electrical and digital logic components.

16. The heating device of claim 1, further comprising an element for reducing turbulence in a flow stream entering the carrier stream inlet of the ion mobility spectrometer, comprising an insert of porous material placed between the heating device housing and the surface of the sample stream inlet at a location proximate to the outlet end of the heating device, wherein the insert fills the gap between the heating device housing and the sample stream inlet surface.

17. The heating device of claim 16, wherein the porous material comprises a meshed metal selected from the group consisting of stainless steel, titanium, nickel, gold and other non-reactive metals having an inherently low vapor pressure characteristic, and further comprising a band of electrically insulating material placed between the insert and the sample stream inlet surface for electrically isolating the sample stream inlet surface from the insert.

18. The heating device of claim 16 wherein the porous material is selected from the group consisting of glass, quartz, teflon, sapphire and other low porosity, low vapor pressure non-chemically reactive non-metallic materials.

19. The heating device of claim 16, wherein the insert is shaped as a round disc with a center opening concentric with the insert outer circumference for attaching the insert to the heating device such that the insert surrounds the heating device housing.

20. The transfer line claim 16, wherein the insert is comprised of a non-metallic material.

21. The heating device of claim 16, wherein the insert is electrically isolated from the ion mobility spectrometer.

22. The heating device of claim 1 for use with an ion mobility spectrometer, wherein the ion mobility spectrometer comprises:
  A. a housing having at least one inlet for communication with a sample media and at least one outlet,
  B. an analyzer positioned within the housing comprising:
    (i) at least first and second longitudinally spaced apart electrodes, the space between the electrodes defining a longitudinal analytical gap, the gap being in communication with a source of carrier gas for flow therethrough,
    (ii) an ionization source juxtaposed with the analytical gap and in communication with the inlet for ionization of sample media,
    (iii) an ion aperture defining an opening between the ionization source and the analytical gap,
    (iv) a third electrode positioned proximate to the ion aperture,
    (v) at least one outlet aperture from the analytical gap remote from the ion aperture,
    (vi) an ion detector for measuring ions from the analytical gap and spaced from the electrodes, and
    (vii) an electrical controller connected to the electrodes for impressing:
      (a) direct current potentials to the first, second and third electrodes, and
      (b) a periodic asymmetrical potential to the first and second electrode, the potentials capable of creating a transverse electric field therebetween during the flow of carrier gas in the analytical gap.

23. The heating device of claim 1, wherein the housing is electrically connected to the ion mobility spectrometer for establishing an electric field at the sample stream inlet of the ion mobility spectrometer.

* * * * *